(12) United States Patent
Yoo et al.

(10) Patent No.: US 10,709,749 B2
(45) Date of Patent: Jul. 14, 2020

(54) COMPOSITION FOR PREVENTING AND TREATING CANCER-RELATED FATIGUE, CONTAINING PROCESSED GINSENG POWDER OR PROCESSED GINSENG EXTRACT HAVING INCREASED GINSENOSIDE CONSTITUENT

(71) Applicant: GREEN CROSS WELLBEING CORPORATION, Yongin-si, Gyeonggi-do (KR)

(72) Inventors: Young Hyo Yoo, Seoul (KR); Jeom Yong Kim, Seoul (KR); Joo Young Kim, Suwon-si (KR); Sun Kyu Park, Suwon-si (KR)

(73) Assignee: GREEN CROSS WELLBEING CORPORATION, Yongin-si, Gyeonggi-Do (KR)

( * ) Notice: Subject to any disclaimer, the term of this patent is extended or adjusted under 35 U.S.C. 154(b) by 618 days.

(21) Appl. No.: 14/915,582

(22) PCT Filed: Aug. 30, 2013

(86) PCT No.: PCT/KR2013/007852
§ 371 (c)(1),
(2) Date: Feb. 29, 2016

(87) PCT Pub. No.: WO2015/030283
PCT Pub. Date: Mar. 5, 2015

(65) Prior Publication Data
US 2016/0213723 A1 Jul. 28, 2016

(51) Int. Cl.
| | | |
|---|---|---|
| *A61K 36/00* | (2006.01) |
| *A61K 36/258* | (2006.01) |
| *A23L 33/105* | (2016.01) |
| *A61K 36/062* | (2006.01) |
| *A61K 31/513* | (2006.01) |
| *A61K 31/704* | (2006.01) |
| *A61K 45/06* | (2006.01) |
| *A61N 5/10* | (2006.01) |
| *C12P 33/20* | (2006.01) |

(52) U.S. Cl.
CPC .......... *A61K 36/258* (2013.01); *A23L 33/105* (2016.08); *A61K 31/513* (2013.01); *A61K 31/704* (2013.01); *A61K 36/062* (2013.01); *A61K 45/06* (2013.01); *A61N 5/10* (2013.01); *C12P 33/20* (2013.01); *A23V 2002/00* (2013.01); *A61K 2236/19* (2013.01)

(58) Field of Classification Search
CPC .............................. A61K 36/25; A61K 36/258
See application file for complete search history.

(56) References Cited

U.S. PATENT DOCUMENTS

| | | | |
|---|---|---|---|
| 2003/0185910 A1 | 10/2003 | Yun et al. |
| 2004/0028671 A1 | 2/2004 | Jin et al. |
| 2005/0031711 A1 | 2/2005 | Park |
| 2005/0222250 A1* | 10/2005 | Rezvani | A61K 31/12 514/461 |
| 2012/0149656 A1 | 6/2012 | Fu et al. |
| 2012/0238743 A1* | 9/2012 | Kim | A61K 8/0212 536/123.1 |
| 2013/0122122 A1 | 5/2013 | Yoo et al. |
| 2014/0294915 A1* | 10/2014 | Barreca | A61K 9/0058 424/440 |
| 2015/0202246 A1* | 7/2015 | Bombardelli | A61K 36/9068 424/479 |

FOREIGN PATENT DOCUMENTS

| | | |
|---|---|---|
| CN | 1477205 A | 2/2004 |
| CN | 1981776 A | 6/2007 |
| CN | 101002785 A | 7/2007 |
| CN | 101612159 A | 12/2009 |
| CN | 103037879 A | 4/2013 |
| EP | 2570132 A2 | 3/2013 |
| JP | 63012300 A | 1/1988 |
| JP | H03-277246 A | 12/1991 |
| JP | H05-009123 A | 1/1993 |
| JP | H06-209773 A | 8/1994 |
| JP | H08-291194 A | 11/1996 |

(Continued)

OTHER PUBLICATIONS

Bonetta, A., & Derelli, R., "Retrospective evaluation of the effect of panax ginseng on fatigue during prostate irradiation," Anticancer Research, 2011, 31(5), pp. 1850-1851, 3 pages.
Office Action dated Jan. 11, 2017, issued in corresponding JP application No. 2016-538479 (with English translation), 8 pages.
Search Report Issued for European Patent Application No. 13892182.0 dated May 2, 2017, 7 pages.
Slichenmyer et al., Anticancer Drugs, Dec. 2, 1991; (6);519-530 (Abstract Only).
Comprehensive clinical 2011 60(11) 2320-2322. (A concise explanation of the relevance of the reference (D4) is provided in the Office Action issued for Japanese Patent Application No. 2017-077232 dated Jan. 16, 2018, thereby satisfying 37 CFR 1.98(a)(3)(i)).
Office Action issued for Japanese Patent Application No. 2017-077232 dated Jan. 16, 2018, along with English translation, 6 pages.

(Continued)

*Primary Examiner* — Qiuwen Mi
(74) *Attorney, Agent, or Firm* — Rothwell, Figg, Ernst & Manbeck, P.C.

(57) ABSTRACT

The present invention relates to a composition for preventing and treating cancer-related fatigue, characterized by containing a new processed ginseng powder or a new processed ginseng extract having an increased amount of a ginsenoside constituent, which was previously minute, by preparing a saponin-decomposing enzyme and subsequently using hydrolysis by the prepared saponin-decomposing enzyme and an organic acid. The composition according to the present invention can be very effectively used for preventing and treating cancer-related fatigue, the most destructive and universal side effect, which is caused by cancer itself or occurs in association with the treatment of cancer.

8 Claims, No Drawings

(56) References Cited

FOREIGN PATENT DOCUMENTS

| | | |
|---|---|---|
| JP | H10-014523 A | 1/1998 |
| JP | H10-099094 A | 4/1998 |
| JP | 2002348245 A | 12/2002 |
| JP | 2003160497 A | 6/2003 |
| JP | 2004519224 A | 7/2004 |
| JP | 2004537565 A | 12/2004 |
| JP | 2005504799 A | 2/2005 |
| JP | 2006502082 A | 1/2006 |
| JP | 2008100999 A | 5/2008 |
| JP | 2008-179620 A | 8/2008 |
| JP | 2009537572 A | 10/2009 |
| JP | 2010132625 A | 6/2010 |
| JP | 2011-512404 A | 4/2011 |
| JP | 2013529899 A | 7/2013 |
| KR | 10-2000-0045694 A2 | 7/2000 |
| KR | 10-2000-0062140 A | 10/2000 |
| KR | 10-2003-0059984 A | 7/2003 |
| KR | 10-2005-0053048 A | 6/2005 |
| KR | 10-2006-0001834 A | 1/2006 |
| KR | 10-2006-0074970 A | 7/2006 |
| KR | 10-0805852 B1 | 2/2008 |
| KR | 10-2008-0106077 A | 12/2008 |
| KR | 10-2009-0037140 A | 4/2009 |
| KR | 10-0992800 B1 | 11/2010 |
| KR | 10-2011-0038758 A | 4/2011 |
| KR | 10-2013-0093331 A | 8/2013 |
| WO | 03010182 A1 | 2/2003 |
| WO | 03024459 A1 | 3/2003 |
| WO | 03056929 A1 | 7/2003 |
| WO | 03086438 A1 | 10/2003 |
| WO | 2005030235 A1 | 4/2005 |
| WO | 2005034963 A1 | 4/2005 |
| WO | 2008155998 A1 | 12/2008 |
| WO | 2008155999 A1 | 12/2008 |
| WO | 2009/104902 A2 | 8/2009 |

OTHER PUBLICATIONS

Tang et al.: "The Anti-fatigue Effect of 20(R)-Ginsenoside Rg3 in Mice by Intranasally Administration," Biol. Pharm. Bull, vol. 31, No. 11, 2008, pp. 2024-2027.

Li, et al. "Advance of research on antitumour activity of ginsenosides", Chinese Journal of Bioprocess Engineering, 2011, 60 (11), 2320-2322.

Japanese Office Action issued for Japanese Patent Application No. 2017-077232 dated Jul. 2, 2019, along with English translation, 6 pages.

Kou Xiao-ge et al., "Influences of ginsenoside Rg3 on immune function and fatigue of the postoperative patients with non-small cell lung cancer", National Medical Frontiers of China, Feb. 2010, vol. 5, No. 3, 2 pages.

First Examination Report issued for Indian patent Application No. 201627010565 dated Feb. 11, 2019, along with English translation (5 pages).

* cited by examiner

COMPOSITION FOR PREVENTING AND TREATING CANCER-RELATED FATIGUE, CONTAINING PROCESSED GINSENG POWDER OR PROCESSED GINSENG EXTRACT HAVING INCREASED GINSENOSIDE CONSTITUENT

CROSS REFERENCE TO RELATED APPLICATIONS

This application is a 35 U.S.C. § 371 National Phase Entry Application from PCT/KR2013/007852, filed on Aug. 30, 2013, and designating the United States, which is incorporated herein by reference in its entirety.

TECHNICAL FIELD

The present invention relates to a composition for preventing and treating cancer-related fatigue, the composition containing a novel processed ginseng powder or processed ginseng extract, of which trace amounts of ginsenoside components are increased by preparing a saponin-decomposing enzyme and then using hydrolysis through the saponin-decomposing enzyme and an organic acid, and provides a composition having an effect of relieving or reducing cancer-related fatigue, which is the most serious among side effects caused by cancer itself or in connection with cancer treatment.

BACKGROUND ART

Cancer-related fatigue (CRF) is one of the most common side effects during or after cancer treatment. Cancer-related fatigue (CRF) is defined, by the National Comprehensive Cancer Network (NCCN), as "a persistent, subjective sense of tiredness related to cancer or cancer treatment that interferes with usual functioning and deteriorates the quality of patient's life". Cancer-related fatigue (CRF) may be differentiated from general fatigue in that it is not relieved by rest and is not primarily caused by physical activity.

Cancer patients describe cancer-related fatigue (CRF) as feeling very severe, chronic, and distressing, and not being relieved by rest. Many studies report that, among the cancer-related side effects, CRF has the most negative impact on the quality of the lives of cancer patient and restricts their normal lives.

It is reported that almost all cancer patients experience the incidence of cancer-related fatigue (CRF) during the cancer treatment, depending on the applied treatment method and period. That is, it is reported that the cancer-related fatigue (CRF) incidence of patients not receiving anticancer treatments is about 75% and the CRF incidence of patients receiving chemotherapy or radiation therapy is higher. With respect to the extent of cancer-related fatigue (CRF), patients having undergone bone marrow transplants and chemotherapy generally shows more severe cancer-related fatigue (CRF) than patients having undergone adjuvant chemotherapy without bone marrow transplants, and patients having undergone adjuvant chemotherapy complain of cancer-related fatigue (CRF) more frequently than patients having undergone radiation therapy (Ikjung, 2010).

Several side effects or general symptoms (e.g., depression, anxiety, pain, nausea, vomiting, insomnia, and anemia), resulting from cancer and cancer treatment, including cancer-related fatigue (CRF), require excessive rest and cause muscular weakness, muscular atrophy, muscular function impairment, and cardiovascular function impairment. Patient's inactivity due to bed rest or the like aggravates the patient's daily living activity.

Most medicine therapies for cancer-related fatigue (CRF) have the intention of treating an allopathic effect rather than approach through cause, and cannot solve problems generated during cancer treatment, such as deterioration in physical strength, loss of muscle mass, and decline in muscle function.

A primary pharmaceutical activity of modafinil, which is a drug associated with cancer-related fatigue (CRF), promotes awareness. Modafinil promotes awareness in models simulating clinical situations, such as obstructive sleep apnea syndrome (English bulldog, sleep-disordered breathing model, Panckeri et al., 1996) and paroxysmal sleep (paroxysmal sleep dug, Shelton et al., 1995) as well as rat (Touret et al., 1995; Edgar and Seidel, 1997), cat, dog (Shelton et al., 1995), and non-human primate (Hernant et al., 1991). In addition, modafinil is a drug that is active in the central nervous system, and is described as a medicine that is useful in the treatment of Parkinson's disease (U.S. Pat. No. 5,180,745), in the protection of cerebral tissue from ischemia (U.S. Pat. No. 5,391,576), in the treatment of urine and urinary incontinence (U.S. Pat. No. 5,401,776), and in the treatment of obstructive sleep apnea syndrome and central origin diseases (U.S. Pat. No. 5,612,379).

Currently, modafinil is in the process of being tested in clinical trials as a cancer-related fatigue (CRF) therapeutic agent by co-administration with docetaxel-based chemotherapy to metastatic breast cancer patients and prostate cancer patients complaining of cancer-related fatigue (CRF), and also by the combined treatment with radiation therapy to solid cancer patients complaining of cancer-related fatigue (CRF) (J. Clin. Oncol. 30, 2012).

The main components of ginseng are ginseng saponines called "ginsenosides", which is designated by specifically differentiating only ginseng saponines from several saponines of plants. Saponines among the ginseng components have pharmaceutical efficacies, such as depressing central nervous system, mental stability, killing pains, improving memory, protecting liver injury, promoting protein and lipid synthesis, anti-diabetic activity, anti-stress activity, promoting the production of antioxidant active substances, immune regulation, inhibiting platelet aggregation, and anti-aging activity, as well as anti-cancer, anti-allergy, and anti-inflammatory activities.

Meanwhile, there are known saponines, such as ginsenosides Rb1, Rb2, and Rc, which are the main components exhibiting pharmaceutical efficacies of ginseng. However, it has been known that compound K and ginsenosides Rh1, Rh2, and Rg3, which are contained in ginseng in trace amounts, are the components which substantially have anti-cancer and anti-allergic activities and inhibit cancer cell metastasis.

With respect to ginsenosides that are known to have an effect on cancer-related fatigue (CRF), ginsenoside Rh2 has been known as a composition for preventing or treating cancer-related fatigue (CRF) (Chinese Patent No. 101612159, 31 Aug. 2011), and it has been reported that Rg3 is not dose-dependent on the fatigue relieving effect in patients having undergone cancer cell removal (Kou Xiaoge et al., National Medical Frontiers of China, 2010, Abstract), but showed an anti-fatigue effect when ginsenoside Rg3 was intranasally administered (Wenyan et al. 2008). However, there has been no patent or research document with respect to a synergetic cancer-related fatigue (CRF) relieving effect depending on the combination of ginsenosides Rh2 and/or Rg3 or the contents thereof.

Unlike general fatigue that is overcome by rest, most medicine therapies for cancer-related fatigue (CRF) have an intention of treating an allopathic effect rather than approach through cause, and cannot solve problems that are generated during cancer treatment, such as deterioration in physical strength, loss of muscle mass, and decline of muscle function. It is recently reported that the dominant mechanisms with respect to the cause of cancer-related fatigue (CRF) in cancer patients having undergone chemotherapy or radiation therapy are increased activities of pro-inflammatory cytokines and deteriorated glycogen synthesis in muscles.

Therefore, the present inventors found that a composition containing a processed ginseng powder or processed ginseng extract, of which trace amounts of ginsenoside components, Rh2 and Rg3, are increased by preparing a saponin-decomposing enzyme and then using hydrolysis through the saponin-decomposing enzyme and an organic acid, is very effective in the prevention and treatment of cancer-related fatigue (CRF), and then the present inventors completed the present invention.

DETAILED DESCRIPTION OF THE INVENTION

Technical Problem

The present inventors found that a processed ginseng powder or processed ginseng extract, of which trace amounts of ginsenoside components are increased by preparing a saponin-decomposing enzyme and then using hydrolysis through the saponin-decomposing enzyme and an organic acid, is helpful in relieving or reducing cancer-related fatigue (CRF).

Therefore, an aspect of the present invention is to provide a composition which is effective in cancer-related fatigue, wherein the composition contains a processed ginseng powder or processed ginseng extract, of which trace amounts of ginsenoside components are increased by preparing a saponin-decomposing enzyme and then using hydrolysis through the saponin-decomposing enzyme and an organic acid.

Technical Solution

The present invention relates to a composition for preventing and treating cancer-related fatigue, the composition containing a processed ginseng powder or processed ginseng extract, of which trace amounts of ginsenoside components are increased by preparing a saponin-decomposing enzyme and then using hydrolysis through the saponin-decomposing enzyme and an organic acid, wherein the processed ginseng powder or processed ginseng extract is prepared by the method according to Korean Patent No. 992800.

In accordance with an aspect of the present invention, there is provided a pharmaceutical composition for preventing or treating cancer-related fatigue, the composition containing a ginseng extract prepared by including:

(a) inoculating an *Aspergillus niger* strain into a medium containing a ginseng powder and bran;
(b) culturing the strain in step (a);
(c) purifying the culture in step (b) through an ultrafiltration membrane;
(d) separating an enzyme from the purified material in step (c);
(e) adding the enzyme in step (d) to a ginseng powder, a red ginseng powder, a ginseng extract, or a red ginseng extract;
(f) fermenting the material after the addition in step (e);
(g) separating the fermented material in step (f) to obtain a supernatant;
(h) concentrating the supernatant in step (g);
(i) allowing the concentrated material in step (h) to react with at least one organic acid selected from the group consisting of acetic acid, lactic acid, citric acid, malic acid, and tartaric acid; and
(j) neutralizing, filtering, purifying, concentrating, and drying the reacted material in step (i).

The composition of the present invention is characterized by containing ginsenosides Rh2 and Rg3, and the composition containing a mixture of Rh2 and Rg3 relieves cancer-related fatigue, caused by anticancer drugs, synergistically and remarkably, compared with a composition containing Rh2 or Rg3 alone.

Each of the contents of ginsenosides Rh2 and Rg3 is preferably 0.2-30 wt %, more preferably 0.5-30 wt %, and most preferably 1-20 wt %.

The processed ginseng powder or processed ginseng extract, of which trace amounts of ginsenoside components are increased by preparing a saponin-decomposing enzyme and then using hydrolysis through the saponin-decomposing enzyme and an organic acid, according to the present invention, relieves cancer-related fatigue caused by existing anticancer drugs, when used in combination with the anticancer drugs.

The existing anticancer drugs include cisplatin, carboplatin, paraplatin, oxaliplatin, nedaplatin, doxorubicin, taxol, docetaxel, tamoxifen, camtobell, adrucil, glivec, etoposide, zometa, oncovin, lupron, gemzar, 5-fluorouracil, and leucovorin.

The processed ginseng powder or processed ginseng extract, of which trace amounts of ginsenoside components are increased by preparing a saponin-decomposing enzyme and then using hydrolysis through the saponin-decomposing enzyme and an organic acid, according to the present invention, is preferably used in combination with an existing drug, in a content of 0.1-1000 parts by weight on the basis of 1 part by weight of the existing anticancer drug. If the content of the processed ginseng powder or processed ginseng extract is within the above range, cancer-related fatigue, which is a side effect caused by the anticancer drug, can be effectively relieved.

The pharmaceutical composition for preventing and treating cancer-related fatigue, the composition containing a processed ginseng powder or processed ginseng extract, of which trace amounts of ginsenoside components are increased by preparing a saponin-decomposing enzyme and then using hydrolysis through the saponin-decomposing enzyme and an organic acid, according to the present invention, may be formulated into various oral or parental administration forms below, but is not limited thereto.

The composition containing a processed ginseng powder or processed ginseng extract, of which trace amounts of ginsenoside components are increased by preparing a saponin-decomposing enzyme and then using hydrolysis through the saponin-decomposing enzyme and an organic acid, according to the present invention, may be manufactured into health supplement food or health functional food in the form of food or drink, for the purpose of preventing or relieving cancer-related fatigue. Here, when used as a food additive, the composition according to the present invention may be added to a raw material in a content of 0.01-30 wt %, and preferably 0.1-10 wt %. The amounts of the active ingredients mixed may be appropriately determined depending on the use purpose. However, when the composition is taken for a long period of time for the purpose of health and sanitation or health control, the amounts of the active ingredients may be below the above ranges. In addition, the active ingredients are not problematic in regards to safety, and thus the contents of the active ingredients may even be above the above ranges. The composition containing a novel processed ginseng powder or processed ginseng extract, of which trace amounts of ginsenoside components are increased by preparing a saponin-decomposing enzyme and then using hydrolysis through the saponin-decomposing enzyme and an organic acid, according to the present invention, may be used together with other foods or food components, and may be appropriately used following the common methods.

Advantageous Effects

The composition of the present invention is directed to a composition containing a novel processed ginseng powder or processed ginseng extract, of which trace amounts of ginsenoside components are increased by preparing a saponin-decomposing enzyme and then using hydrolysis through the saponin-decomposing enzyme and an organic acid, and the composition of the present invention is effective in the prevention or treatment of cancer-related fatigue.

The composition containing a novel processed ginseng powder or processed ginseng extract, of which trace amounts of ginsenoside components are increased by preparing a saponin-decomposing enzyme and then using hydrolysis through the saponin-decomposing enzyme and an organic acid, of the present invention, contains both ginsenosides Rh2 and Rg3 with increased amounts, and thus the composition synergistically exhibits an excellent effect on the prevention or treatment of cancer-related fatigue, compared with a composition containing Rh2 or Rg3 alone.

Furthermore, the composition of the present invention exhibits an excellent effect of preventing and treating, relieving or reducing cancer-related fatigue.

Method for Carrying Out the Invention

The present invention relates to a composition for preventing and treating cancer-related fatigue, the composition containing a novel processed ginseng powder or processed ginseng extract, of which trace amounts of ginsenoside components are increased by preparing saponin-decomposing enzyme and then using hydrolysis through the saponin-decomposing enzyme and an organic acid, wherein the processed ginseng powder or processed ginseng extract is prepared by the method according to Korean Patent No. 992800.

Hereinafter, the present invention will be described in more detail through specific examples.

However, the scope of the present invention is not limited to only examples, and can be modified and implemented by a person skilled in the art within the technical scope of the present invention, and it would be obvious to a person skilled in the art that this modification and implementation fall within the scope of the present invention.

Comparative Example 1

Preparing Ginseng Powder 200 g of 6-year-old ginseng was dried under hot air, followed by pulverization, to give 60 g of a ginseng powder.

Comparative Example 2

Preparing Ginseng Concentrate 200 g of 6-year-old ginseng was dried under hot air, and added with 1 L of 70% alcohol, followed by extraction with stirring at 70° C. for 8 h, filtration, and concentration, to give 50 g of a ginseng concentrate.

Comparative Example 3

Preparing Powered Ginseng Concentrate 200 g of 6-year-old ginseng was dried under hot air, and added with 1 L of 70% alcohol, followed by extraction with stirring at 70° C. for 8 h, filtration, concentration, and drying, to give 30 g of a powdered ginseng concentrate.

Comparative Example 4

Preparing Red Ginseng Powder 200 g of 6-year-old ginseng was steamed at 98° C. for 1 h and then dried, followed by pulverization, to give 40 g of a red ginseng powder.

Comparative Example 5

Preparing Red Ginseng Concentrate 200 g of 6-year-old ginseng was steamed at 98° C. for 1 h, followed by drying, and 1 L of 70% alcohol was added thereto, followed by extraction with stirring at 70° C. for 8 h, filtration, and concentration, to give 30 g of a red ginseng concentrate.

Comparative Example 6

Preparing Powdered Red Ginseng Concentrate 200 g of 6-year-old ginseng was steamed at 98° C. for 1 h, followed by drying, and 1 L of 70% alcohol was added thereto, followed by extraction with stirring at 70° C. for 8 h, filtration, concentration, and drying, to give 25 g of a powdered red ginseng concentrate.

Comparative Example 7

Preparing Ginseng Powder+0.2% Rh2+0.3% Rg3

0.2 g of Rh2 and 0.3 g of Rg3 were mixed with 99.5 g of the ginseng powder of comparative example 1.

Comparative Example 8

Preparing Red Ginseng Powder+0.2% Rh2+0.3% Rg3

0.2 g of Rh2 and 0.3 g of Rg3 were mixed with 99.5 g of the red ginseng powder of comparative example 4.

Comparative Example 9

Preparing Red Ginseng Powder+1% Rh2

1 g of Rh2 was mixed with 99 g of the red ginseng powder of comparative example 4.

Comparative Example 10

Preparing Red Ginseng Powder+1% Rg3

1 g of Rg3 was mixed with 99 g of the red ginseng powder of comparative example 4.

Comparative Example 11

Preparing Red Ginseng Powder+0.5% Rh2+0.5% Rg3

0.5 g of Rh2 and 0.5 g of Rg3 were mixed with 99 g of the red ginseng powder of comparative example 4.

Comparative Example 12

Preparing Modafinil

Modafinil (100 mg/kg. B. W) was mixed with PBS, and the mixture was orally administered at 100 μl per day.

Example 1

Preparing Processed Ginseng Powder Using Ginseng Powder 250 g of a ginseng powder and 750 g of bran were sterilized using a high-pressure steam sterilizer at 121° C. under 1.5 atmospheric pressure. The sterilized medium was mixed with 2 L of sterilized water, and then an *Aspergillus niger* suspension ($5 \times 10^5$ spores/g of medium weight) was cultured at 28° C. for 7 days. Upon the completion of the culturing, a 0.02 M sodium acetate buffer was added and mixed with the culture, followed by filtration. The filtered culture was filtered and concentrated using an ultrafiltration membrane (100 KDa or higher), to give 60 g of an enzyme liquid. 30 g of the enzyme liquid was added to 200 g of the ginseng powder of comparative example 1, followed by culturing at 28° C. for 18 h, and then alcohol was added thereto, leading to enzyme precipitation and supernatant concentration. 2 L of purified water was added to 200 g of the concentrated material, and then 250 g of citric acid was added, followed by stirring at 50° C. for 18 h. Upon the completion of the reaction, 70% alcohol was added, followed by filtration, concentration, and drying, to give 200 g of a processed ginseng powder.

Example 2

Preparing Processed Ginseng Concentrate Using Ginseng Concentrate 250 g of a ginseng powder and 750 g of bran were sterilized using a high-pressure steam sterilizer at 121° C. under 1.5 atmospheric pressure. The sterilized medium was mixed with 2 L of sterilized water, and then an *Aspergillus niger* suspension ($5 \times 10^5$ spores/g of medium weight) was inoculated thereinto, followed by culturing at 28° C. for 7 days. Upon the completion of the culturing, a 0.02 M sodium acetate buffer was added and mixed with the culture, followed by filtration. The filtered culture was filtered and concentrated using an ultrafiltration membrane (100 KDa or higher), to give 60 g of an enzyme liquid. 30 g of the enzyme liquid was added to 200 g of the ginseng concentrate of comparative example 2, followed by culturing at 28° C. for 18 h, and then alcohol was added thereto, leading to enzyme precipitation and supernatant concentration. 2 L of purified water was added to 200 g of the concentrated material, and then 250 g of citric acid was added, followed by stirring at 50° C. for 18 h. Upon the completion of the reaction, 70% alcohol was added, followed by filtration and concentration, to give 190 g of a processed ginseng concentrate.

Example 3

Preparing Processed Powdered Ginseng Concentrate Using Powdered Ginseng Concentrate 250 g of a ginseng powder and 750 g of bran were sterilized using a high-pressure steam sterilizer at 121° C. under 1.5 atmospheric pressure. The sterilized medium was mixed with 2 L of sterilized water, and then an *Aspergillus niger* suspension ($5 \times 10^5$ spores/g of medium weight) was inoculated thereinto, followed by culturing at 28° C. for 7 days. Upon the completion of the culturing, a 0.02 M sodium acetate buffer was added and mixed with the culture, followed by filtration. The filtered culture was filtered and concentrated using an ultrafiltration membrane (100 KDa or higher), to give 60 g of an enzyme liquid. 30 g of the enzyme liquid was added to 200 g of the powdered ginseng concentrate of comparative example 3, followed by culturing at 28° C. for 18 h, and then alcohol was added thereto, leading to enzyme precipitation and supernatant concentration. 2 L of purified water was added to 200 g of the concentrated material, and then 250 g of acetic acid was added, followed by stirring at 50° C. for 8 h. Upon the completion of the reaction, 70% alcohol was added, followed by filtration, concentration, and drying, to give 195 g of a processed powdered ginseng concentrate.

Example 4

Preparing Processed Red Ginseng Powder Using Red Ginseng Powder 250 g of a ginseng powder and 750 g of bran were sterilized using a high-pressure steam sterilizer at 121° C. under 1.5 atmospheric pressure. The sterilized medium was mixed with 2 L of sterilized water, and then an *Aspergillus niger* suspension ($5 \times 10^5$ spores/g of medium weight) was cultured at 28° C. for 7 days. Upon the completion of the culturing, a 0.02 M sodium acetate buffer was added and mixed with the culture, followed by filtration. The filtered culture was filtered and concentrated using an ultrafiltration membrane (100 KDa or higher), to give 60 g of an enzyme liquid. 30 g of the enzyme liquid was added to 200 g of the red ginseng powder of comparative example 4, followed by culturing at 28° C. for 18 h, and then alcohol was added thereto, leading to enzyme precipitation and supernatant concentration. 2 L of purified water was added to 200 g of the concentrated material, and then 250 g of acetic acid was added, followed by stirring at 50° C. for 8 h. Upon the completion of the reaction, 70% alcohol was added, followed by filtration, concentration, and drying, to give 195 g of a processed red ginseng powder.

Example 5

Preparing Processed Red Ginseng Concentrate Using Red Ginseng Concentrate 250 g of a ginseng powder and 750 g of bran were sterilized using a high-pressure steam sterilizer at 121° C. under 1.5 atmospheric pressure. The sterilized medium was mixed with 2 L of sterilized water, and then an *Aspergillus niger* suspension ($5\times10^5$ spores/g of medium weight) was inoculated thereinto, followed by culturing at 28° C. for 7 days. Upon the completion of the culturing, a 0.02 M sodium acetate buffer was added and mixed with the culture, followed by filtration. The filtered culture was filtered and concentrated using an ultrafiltration membrane (100 KDa or higher), to give 60 g of an enzyme liquid. 30 g of the enzyme liquid was added to 200 g of the red ginseng concentrate of comparative example 5, followed by culturing at 28° C. for 18 h, and then alcohol was added thereto, leading to enzyme precipitation and supernatant concentration. 2 L of purified water was added to 200 g of the concentrated material, and then 250 g of citric acid was added, followed by stirring at 50° C. for 18 h. Upon the completion of the reaction, 70% alcohol was added, followed by filtration and concentration, to give 190 g of a processed red ginseng concentrate.

Example 6

Preparing Processed Powdered Red Ginseng Concentrate Using Powdered Red Ginseng Concentrate 250 g of a ginseng powder and 750 g of bran were sterilized using a high-pressure steam sterilizer at 121° C. under 1.5 atmospheric pressure. The sterilized medium was mixed with 2 L of sterilized water, and then an *Aspergillus niger* suspension ($5\times10^5$ spores/g of medium weight) was inoculated thereinto, followed by culturing at 28° C. for 7 days. Upon the completion of the culturing, a 0.02 M sodium acetate buffer was added and mixed with the culture, followed by filtration. The filtered culture was filtered and concentrated using an ultrafiltration membrane (100 KDa or higher), to give 60 g of an enzyme liquid. 30 g of the enzyme liquid was added to 200 g of the powdered red ginseng concentrate of comparative example 6, followed by culturing at 28° C. for 18 h, and then alcohol was added thereto, leading to enzyme precipitation and supernatant concentration. 2 L of purified water was added to 200 g of the concentrated material, and then 250 g of acetic acid was added, followed by stirring at 50° C. for 8 h. Upon the completion of the reaction, 70% alcohol was added, followed by filtration, concentration, and drying, to give 195 g of a processed powdered red ginseng concentrate.

Table 1 below shows contents of ginsenoside Rh2 and Rg3 contained in the preparations of the examples and comparative examples, which were analyzed by the method disclosed in Korean Patent No. 992800. It was confirmed that the novel processes ginseng powder or processed ginseng extract, corresponding to examples 1 to 6 of the present invention, of which trace amounts of ginsenoside components are increased by preparing a saponin-decomposing enzyme for the ginseng powder and red ginseng powder and then using hydrolysis through the prepared saponin-decomposing enzymes and an organic acid, contained large amounts of Rh2 and Rg3 compared with a ginseng powder and a red ginseng powder, which are reactive target materials thereof. Comparative examples 7 to 11 were prepared by simply adding Rh2 and Rg3 to a ginseng powder and a red ginseng powder, which were not hydrolysis-treated with a saponin-decomposing enzyme and an organic acid, such that the contents of Rh2 and Rg3 were the same as those in examples of the present invention, for the comparison of cancer-related fatigue relieving effect.

TABLE 1

Contents of ginsenosides Rh2 and Rg3 contained in examples and comparative examples of the present inventin

| Classification | Content (wt %) | |
|---|---|---|
| | Rh2 | Rg3 |
| Example 1 (processed ginseng powder) | 0.2 | 0.3 |
| Example 2 (processed ginseng concentrate) | 3 | 3 |
| Example 3 (processed powdered ginseng concentrate) | 12 | 18 |
| Example 4 (processed red ginseng powder) | 0.6 | 0.8 |
| Example 5 (processed red ginseng concentrate) | 1 | 3 |
| Example 6 (processed powdered red ginseng concentrate) | 5 | 10 |
| Comparative example 1 (ginseng powder) | <0.01 | <0.01 |
| Comparative example 2 (giseng concentrate) | <0.5 | <0.01 |
| Comparative example 3 (powdered ginseng concentrate) | <0.5 | <0.01 |
| Comparative example 4 (red ginseng powder) | <0.01 | <0.01 |
| Comparative example 5 (red ginseng concentrate) | <0.5 | <0.01 |
| Comparative example 6 (powdered red ginseng concentrate) | <0.5 | <0.01 |
| Comparative example 7 (ginseng powder 99.5 g + Rh2 0.2 g + Rg3 0.3 g) | 0.2 | 0.3 |
| Comparative example 8 (red ginseng powder 99.5 g + Rh2 0.2 g + Rg3 0.3 g) | 0.2 | 0.3 |
| Comparative example 9 (red ginseng powder 99 g + Rh2 1 g) | 1 | <0.01 |
| Comparative example 10 (red ginseng powder 99 g + Rg3 1 g) | <0.01 | 1 |
| Comparative example 11 (red ginseng powder 99 g + Rh2 0.5 g + Rg3 0.5 g) | 0.5 | 0.5 |

Test Example 1

Effect of Composition for Relieving Cancer-Caused Fatigue 6-wk-old Balb/c-nu/nu female mice weighing 20±2 g were obtained from Orient Inc., and housed in animal rooms under a temperature of 23±1° C., relative humidity of 55±15%, and 12-hour light/dark illumination cycle. The mice were acclimated with free access to a feed (Orient Inc.) for 1 week, and symptoms were observed to the naked eyes. After acclamation for 1 week, 1000 µl of HT-29 cells ($5\times10^6$ cells/mouse) were subcutaneously injected into the flank of the Balb/c nu/nu mouse, and the mice were observed by the naked eyes. The mice were randomized into groups when the tumor size reached 150 mm$^2$, and then drug administration was initiated. Voluntary motor activity (running wheel activity) and forced motor activity (swimming test) were measured after the administration of anticancer drug and drugs was completed, and the amount of glycogen synthesized in the muscle was assayed through an ELISA kit after the tissue taken from the femoral region on the final date of autopsy was homogenized.

Running wheel activity (Running distance=meter/10 min)

The voluntary motor activity was measured as the parameter of cancer-related fatigue (CRF) through running wheel activity. The number of wheels ran for a total of 10 min on 300 θ wheel was counted, and running distance was calculated.

Running distance=circumference(30 cm×3.14)×number of wheels/10 min

Swimming Test

A transparent temperature-constant water bath (500 mm×500 mm×400 mm), which maintained the designated temperature and water level, was filled with warm water (23±1° C.)., and then the animals were subjected to forced swimming (FS). The swimming time immediately after total exhaustion was recorded.

Rate of Increase (%)

$$\frac{\text{Mean of group treated with example or comparative example} - \text{Mean of control group}}{\text{Mean of } normgal \text{ group} - \text{Mean of control group}} \times 100$$

All the examples and comparative examples were diluted in phosphate buffered saline (PBS) according to the dosage, and compulsorily administered to the animals using needle for oral administration (Sonde). The dosage was diluted in PBS to 100 mg/kg of body weight, and the dosage was calculated such that 100 μl/20 g was administered depending on the weight measured on the day of administration. Test materials were administered at the same time once per day, at 10 AM, for 4 weeks, for the examples and comparative examples. The groups for evaluation in the present test are shown in table 2.

For tests of significance for all test examples below, p-value comparison was conducted through Student's T-test with significant level of 0.05.

: p<0.05 vs Normal group *: p<0.05 vs Control group
: p<0.01 vs Normal group **: p<0.01 vs Control group
: p<0.001 vs Normal group ***: p<0.001 vs Control group

TABLE 2

Test group and drug administration method in test example 1

| Test group | Administration method |
|---|---|
| Normal | PBS/oral admininstration |
| Control (HT-29 cells only) | PBS/oral admininstration |
| Examples 1-6 Comparative examples 1-12 | Example/Comparative example oral administration (Drug was diluted in PBS to 100 mg/kg of body weight, and orally administered at 100 μl every day for 4 weeks.) |

Table 3 below shows results of test example 1 above, and indicates comparison results of voluntary motor activity by cancer obtained by distance traveled for 10 min after examples and comparative examples were administered to animal models xenografted with HT-29 colon cancer cell line. Table 4 shows comparison results of forced motor activity by cancer by the swimming time. The processed ginseng powder or processed ginseng extract, corresponding to examples 1 to 6 of the present invention, of which traces amounts of ginsenoside components are increased by preparing a saponin-decomposing enzyme, for the ginseng powder and red ginseng powder and then using hydrolysis through the saponin-decomposing enzyme and an organic acid, showed a voluntary motor activity increase rate of 62.6-96.2% and a forced motor activity increase rate of 63.0-98.0%, which were greater than the voluntary motor activity increase rate and the forced motor activity increase rate of 3.2-18.8% by the ginseng powder and the red ginseng powder of comparative examples 1 to 6, corresponding to reactive target materials of examples 1 to 6 of the present invention, thus indicating excellent activity increase rates through the relief of cancer-related fatigue. In addition, the processed ginseng powder or processed ginseng extract of examples 1 to 6 of the present invention, showed excellent activity increase rates through the relief of cancer-related fatigue, compared with voluntary and forced motor activity increase rates of 20.8-30.6% of comparative examples 7 and 8, which were prepared by adding Rh2 and Rg3 to the ginseng powder and the red ginseng powder of comparative examples 1 to 4 such that the Rh2 and Rg3 contents were increased to 0.2 wt % and 0.3 wt %, respectively. It can be seen from these results that the activity increase effect through the relief of cancer-related fatigue by the processed ginseng or processed ginseng extract was synergistic together with other active ingredients other than Rh2 and Rg3. Meanwhile, comparative examples 9 to 11 are compositions prepared by further adding 1 g of Rh2, 1 g of Rg3, and (0.5 g of Rh2+0.5 g of Rg3) to 99 g of the red ginseng powder. Comparative Example 11 (0.5 wt % of Rh2+0.5 wt % of Rg3) showed excellent treatment effects on cancer-related fatigue, compared with comparative example 9 (containing 1 wt % of Rh2) and comparative example 10 (containing 1 wt % of Rg3). These results can confirm that the co-administration of Rh2 and Rg3 had a synergistic effect in relieving, reducing or treating cancer-related fatigue than the administration of Rh2 or Rg3 alone.

TABLE 3

Comparative evauation of voluntary motor activity by cancer

| Classification | Running distance for 10 min (meter/10 min) | Increase (%) in running distance for 10 min, compared with control |
|---|---|---|
| Normal | 96.5 ± 6.8 | — |
| Xenograft Control) | 61.9 ± 3.3### | — |
| Example 1 | 83.5 ± 3.5** | 62.6 |
| Example 2 | 93.0 ± 3.1*** | 89.9 |
| Example 3 | 95.2 ± 2.4*** | 96.2 |
| Example 4 | 88.1 ± 2.4*** | 75.7 |
| Example 5 | 91.1 ± 2.5*** | 84.4 |
| Example 6 | 93.5 ± 2.7*** | 91.3 |
| Comparative example 1 | 63.0 ± 2.4 | 3.2 |
| Comparative example 2 | 64.3 ± 3.2 | 6.9 |
| Comparative example 3 | 67.6 ± 2.5 | 16.5 |
| Comparative example 4 | 65.5 ± 3.6 | 10.4 |
| Comparative example 5 | 68.4 ± 2.8 | 18.8 |
| Comparative example 6 | 67.1 ± 3.8 | 15.0 |
| Comparative example 7 | 71.2 ± 4.8 | 26.8 |
| Comparative example 8 | 72.5 ± 4.2 | 30.6 |
| Comparative example 9 | 71.3 ± 4.1 | 27.1 |
| Comparaive example 10 | 11.9 ± 2.9 | 28.9 |
| Comparative example 11 | 76.1 ± 3.7* | 41.0 |

TABLE 3-continued

Comparative evauation of voluntary motor activity by cancer

| Classification | Running distance for 10 min (meter/10 min) | Increase (%) in running distance for 10 min, compared with control |
|---|---|---|
| Comparative example 12 | 80.1 ± 1.9** | 52.6 |

TABLE 4

Comparative evauation of forced motor activity by cancer

| Classification | Total swimming time (sec) | Increase (%) in swimming time, compared with control |
|---|---|---|
| Normal | 909.0 ± 76.5 | — |
| Xenograft (Control) | 423.6 ± 50.9### | — |
| Example 1 | 729.4 ± 67.4** | 63 |
| Example 2 | 855.3 ± 57.2*** | 88.9 |
| Example 3 | 899.5 ± 67.3*** | 98.0 |
| Example 4 | 825.3 ± 33.7*** | 82.8 |
| Example 5 | 845.1 ± 75.5*** | 86.8 |
| Example 6 | 867.3 ± 38.0*** | 91.4 |
| Comparative example 1 | 448.3 ± 61.3 | 5.1 |
| Comparative example 2 | 465.5 ± 52.4 | 8.6 |
| Comparative example 3 | 485.8 ± 41.1 | 12.8 |
| Comparative example 4 | 472.3 ± 54.9 | 10.0 |
| Comparative example 5 | 489.6 ± 36.7 | 13.6 |
| Comparative example 6 | 493.9 ± 38.2 | 14.5 |
| Comparative example 7 | 524.9 ± 47.1 | 20.8 |
| Comparative example 8 | 530.2 ± 51.1 | 21.9 |
| Comparative example 9 | 535.1 ± 55.8 | 23.0 |
| Comparative example 10 | 550.3 ± 57.7 | 26.1 |
| Comparative example 11 | 635.3 ± 67.5* | 43.6 |
| Comparative example 12 | 731.8 ± 60.1** | 63.5 |

Test Example 2

Effect of Fatigue Relieving Composition by Anticancer Drug

Evaluation was conducted in the same conditions as in test example 1, except that all the examples and comparative examples were compared in the conditions of treatment with an anticancer drug. The treatment with 5-FU as an anticancer drug was conducted at 30 mg/kg three times per week. The groups for evaluation in the present test example are shown in table 5.

TABLE 5

Test group and drug administration method in test example 2

| Test group | Administration method | |
|---|---|---|
| Normal | PBS/oral administration | |
| HT-29 cells only | 0.9% NaCl/oral administration | PBS/oral administration |
| 5-FU - Control | 5-FU intraperitoneal administration (30 mg/kg/BW, 3 days per week) | |
| 5-FU + Example 1 | | Example/Comparative example oral administration (Drug was diluted in PBS to 100 mg/kg of body weight, and orally administered at 100 μl every day for 4 weeks.) |
| 5-FU + Example 2 | | |
| 5-FU + Example 3 | | |
| 5-FU + Example 4 | | |
| 5-FU + Example 5 | | |
| 5-FU + Example 6 | | |
| 5-FU + Comparative example 1 | | |
| 5-FU + Comparative example 4 | | |
| 5-FU + Comparative example 7 | | |
| 5-FU + Comparative example 9 | | |
| 5-FU + Comparative example 10 | | |
| 5-FU + Comparative example 11 | | |
| 5-FU + Comparative example 12 | | |

Table 6 shows results of test example 2 above, and indicates comparison results of the amount of glycogen synthesized in the muscle taken from the femoral region on the final date of autopsy, after the anticancer drug and each of the example and comparative example were co-administered to the animal models xenografted with HT-29 colon cancer cell line for 4 weeks. As a result, the Xenograft group xenografted with colon cancer showed an amount of glycogen synthesis, which was reduced by 39.2%, compared with normal groups, and the control group administered with anticancer drug showed a reduction of 51.4% compared with the normal groups. However, it can be confirmed that the co-administration of examples 1-6 together with the anticancer drug resulted in a significant increase in the amount of glycogen synthesis, compared with the control group administered with the anticancer drug, and the group co-administered with the comparative example (modafinil) did not show any great change compared with examples. The increases in the amount of glycogen synthesis for the respective examples and comparative examples are shown in table 6.

TABLE 6

Amount of glycogen synthesized in muscle taken from animal femoral region in test example 2

| Classification | | Mean Muscle Glycogen (mg/g) | Increase (%) in glycogen synthesis, compared with control |
|---|---|---|---|
| Normal | | 7.4 ± 0.5 | — |
| Xenograft | | 4.5 ± 0.2### | — |
| 5-FU (30 mg/kg, 3 days per week) | Control | 3.6 ± 0.3### | — |
| | Example 1 | 5.9 ± 0.1** | 60.5 |
| | Example 2 | 6.5 ± 0.5*** | 78.5 |
| | Example 3 | 6.7 ± 0.5*** | 89.5 |
| | Example 4 | 6.9 ± 0.6*** | 75.3 |
| | Example 5 | 5.5 ± 0.2*** | 77.5 |

TABLE 6-continued

Amount of glycogen synthesized in muscle taken from animal femoral region in test example 2

| Classification | Mean Muscle Glycogen (mg/g) | Increase (%) in glycogen synthesis, compared with control |
|---|---|---|
| Example 6 | 6.0 ± 0.4*** | 82.4 |
| Comparative example 1 | 4.0 ± 0.5 | 10.3 |
| Comparative example 4 | 4.1 ± 0.7 | 13.1 |
| Comparative example 7 | 4.3 ± 0.3 | 18.4 |
| Comparative example 9 | 4.8 ± 0.6 | 31.6 |
| Comparative example 10 | 4.7 ± 0.8 | 29 |
| Comparative example 11 | 5.3 ± 0.3* | 44.7 |
| Comparative example 12 | 4.3 ± 0.5 | 18.4 |

Test Example 3

Effect of Fatigue Relieving Composition by Radiation Treatment

Evaluation was conducted in the same conditions as in test example 1, except that all the examples and comparative examples were compared in the conditions of radiation treatment. The radiation treatment was conducted at 10 Gy three times per week. The groups for evaluation in the present test example are shown in table 7.

TABLE 7

Test group and drug administration method in test example 3

| Test group | Admininstration method | |
|---|---|---|
| Normal | PBS/oral administration | |
| HT cells only | 0.9% NaCl/ intraperitoneal administration | PBS/oral admininstration |
| radio therapy - Control | Radio therapy (10 Gy, 3 days per week) | |
| radio therapy + Example 1 | | Example/Comparative example, oral administration (100 μl/every day/4 weeks) |
| radio therapy + Example 2 | | |
| radio therapy + Example 3 | | |
| radio therapy + Example 4 | | |
| radio therapy + Example 5 | | |
| radio therapy + Example 6 | | |
| radio therapy + Comparative example 1 | | |
| radio therapy + Comparative example 4 | | |
| radio therapy + Comparative example 7 | | |
| radio therapy + Comparative example 9 | | |
| radio therapy + Comparative example 10 | | |
| radio therapy + Comparative example 11 | | |
| radio therapy + Comparative example 12 | | |

Table 8 shows results of test example 3 above, and indicates comparison results of the amount of glycogen synthesized in the muscle taken from the femoral region on the final date of autopsy, after the radiation treatment and each of the example and comparative example were co-treated to the animal models xenografted with HT-29 colon cancer cell line for 4 weeks. As a result, the Xenograft group xenografted with colon cancer showed an amount of glycogen synthesis, which was reduced by 36.5%, compared with normal groups, and the control group treated with radiation showed a reduction of 51.4% compared with the normal groups. However, it can be confirmed that the combined use of examples 1-6 together and the radiation treatment resulted in a significant increase in the amount of glycogen synthesis, compared with the control group treated with radiation, and the group co-treated with comparative examples 1, 4, 7, 9, 10, 11, and 12 (modafinil) did not show any great change compared with examples. The increases in the amount of glycogen synthesis for the respective examples and comparative examples are shown in table 8.

TABLE 8

Amount of glycogen synthesized in muscle taken from animal femoral region in test example 3

| Classification | | Mean Muscle Glycogen (mg/g) | Increase (%) in glycogen synthesis, compared with control |
|---|---|---|---|
| Normal | | 7.4 ± 0.5 | — |
| Xenograft | | 4.7 ± 0.2### | — |
| Radio therapy (10Gy, 3 days per week) | Control | 3.6 ± 0.3### | — |
| | Example 1 | 5.5 ± 0.2* | 50.0 |
| | Example 2 | 5.9 ± 0.3** | 60.5 |
| | Example 3 | 6.4 ± 0.4*** | 73.6 |
| | Example 4 | 6.2 ± 0.4*** | 68.4 |
| | Example 5 | 5.9 ± 0.1** | 60.5 |
| | Example 6 | 6.1 ± 0.4*** | 65.8 |
| | Comparative example 1 | 3.8 ± 0.3 | 5.3 |
| | Comparative example 4 | 3.9 ± 0.5 | 7.9 |
| | Comparative example 7 | 4.2 ± 0.3 | 15.8 |
| | Comparative example 9 | 4.2 ± 0.3 | 15.8 |
| | Comparative example 10 | 4.3 ± 0.5 | 18.4 |
| | Comparative example 11 | 4.7 ± 0.4 | 29.0 |
| | Comparative example 12 | 3.9 ± 0.2 | 7.9 |

The invention claimed is:

1. A method for relieving or reducing cancer-related fatigue in a patient suffering from the cancer-related fatigue, comprising administering to the patient an effective amount of a composition containing a ginseng extract having increased contents of ginsenosides Rg3 and Rh2, wherein the ginseng extract contains ginsenosides Rh2 and Rg3 in contents of 0.5-30 wt %, respectively, wherein the ginseng extract having increased contents of ginsenosides Rg3 and Rh2 is prepared by:

(a) inoculating an *Aspergillus niger* strain into a medium containing a ginseng powder and bran;
(b) culturing the strain in step (a) to produce a cultured material;
(c) purifying the cultured material in step (b) through an ultrafiltration membrane to produce a purified material;
(d) separating an enzyme from the purified material in step (c);
(e) adding the enzyme in step (d) to a ginseng powder, a red ginseng powder, a *ginseng* extract, or a red ginseng extract;
(f) fermenting the material after the addition in step (e) to produce a fermented material;
(g) separating the fermented material in step (f) to obtain a supernatant;
(h) concentrating the supernatant in step (g);
(i) reacting the concentrated material in step (h) with at least one organic acid selected from the group consisting of acetic acid, lactic acid, citric acid, malic acid, and tartaric acid to produce a reacted material; and
(j) neutralizing, filtering, purifying, concentrating, and drying the reacted material in step (i) to obtain the ginseng extract having increased contents of ginsenosides Rg3 and Rh2;
wherein said administering relieves or reduces the cancer-related fatigue in said patient suffering from cancer-related fatigue.

2. The method of claim 1, wherein the composition is administered to the patient in combination with radiation therapy.

3. The method of claim 1, wherein the composition is administered to the patient in combination with an anticancer drug.

4. The method of claim 3, wherein the anticancer drug is at least one selected from cisplatin, carboplatin, paraplatin, oxaliplatin, nedaplatin, doxorubicin, taxol, docetaxel, tamoxifen, belotecan, fluorouracil, glivec, etoposide, zometa, oncovin, lupron, gemzar, and leucovorin.

5. The method of claim 3, wherein the ginseng extract having increased contents of ginsenosides Rg3 and Rh2 is administered in an amount of 0.1-1000 parts by weight based on 1 part by weight of the anticancer agent that is administered.

6. A method for reducing cancer cachexia or weight loss due to anticancer drug therapy or radiation therapy in a patient suffering from the cancer cachexia or weight loss due to anticancer drug therapy or radiation therapy, comprising administering to the patient an effective amount of a composition containing a ginseng extract having increased contents of ginsenosides Rg3 and Rh2, wherein the ginseng extract contains ginsenosides Rh2 and Rg3 in contents of 0.5-30 wt %, respectively, wherein the ginseng extract having increased contents of ginsenosides Rg3 and Rh2 is prepared by:
(a) inoculating an *Aspergillus niger* strain into a medium containing a ginseng powder and bran;
(b) culturing the strain in step (a) to produce a cultured material;
(c) purifying the cultured material in step (b) through an ultrafiltration membrane to produce a purified material;
(d) separating an enzyme from the purified material in step (c);
(e) adding the enzyme in step (d) to a ginseng powder, a red ginseng powder, a ginseng extract, or a red ginseng extract;
(f) fermenting the material after the addition in step (e) to produce a fermented material;
(g) separating the fermented material in step (f) to obtain a supernatant;
(h) concentrating the supernatant in step (g);
(i) reacting the concentrated material in step (h) with at least one organic acid selected from the group consisting of acetic acid, lactic acid, citric acid, malic acid, and tartaric acid to produce a reacted material; and
(j) neutralizing, filtering, purifying, concentrating, and drying the reacted material in step (i) to obtain the ginseng extract having increased contents of ginsenosides Rg3 and Rh2;
wherein said administering reduces cancer cachexia or weight loss due to anticancer drug therapy or radiation therapy in said patient suffering from the cancer cachexia or weight loss due to anticancer drug therapy or radiation therapy.

7. A method for reducing loss of muscle mass in a cancer patient suffering from the loss of muscle mass, comprising administering to the cancer patient an effective amount of a composition containing a ginseng extract having increased contents of ginsenosides Rg3 and Rh2, wherein the ginseng extract contains ginsenosides Rh2 and Rg3 in contents of 0.5-30 wt %, respectively, wherein the ginseng extract having increased contents of ginsenosides Rg3 and Rh2 is prepared by:
(a) inoculating an *Aspergillus niger* strain into a medium containing a ginseng powder and bran;
(b) culturing the strain in step (a) to produce a cultured material;
(c) purifying the cultured material in step (b) through an ultrafiltration membrane to produce a purified material;
(d) separating an enzyme from the purified material in step (c);
(e) adding the enzyme in step (d) to a ginseng powder, a red ginseng powder, a ginseng extract, or a red ginseng extract;
(f) fermenting the material after the addition in step (e) to produce a fermented material;
(g) separating the fermented material in step (f) to obtain a supernatant;
(h) concentrating the supernatant in step (g);
(i) reacting the concentrated material in step (h) with at least one organic acid selected from the group consisting of acetic acid, lactic acid, citric acid, malic acid, and tartaric acid to produce a reacted material; and
(j) neutralizing, filtering, purifying, concentrating, and drying the reacted material in step (i) to obtain the ginseng extract having increased contents of ginsenosides Rg3 and Rh2;
wherein said administering reduces loss of muscle mass in said cancer patient-suffering from the loss of muscle mass.

8. The method of claim 7, wherein said administering is to a patient being treated with radiotherapy or 5-FU, and wherein administering the composition increases glycogen synthesis in the patient by at least 50% compared to a patient treated with radiotherapy or 5-FU that is not administered the composition.

* * * * *